Figure 1:
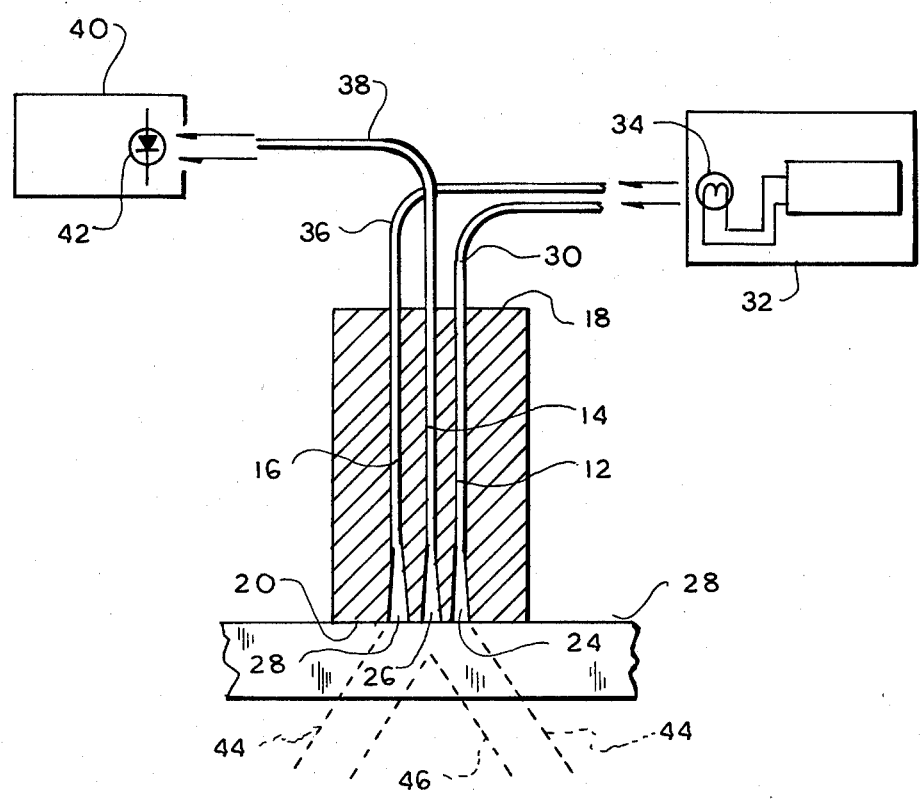

United States Patent [19]

Apothaker

[11] 4,379,225
[45] Apr. 5, 1983

[54] FIBEROPTIC HEAD WITH FIBER BUNDLES HAVING DIFFERENT NUMERICAL APERTURES

[75] Inventor: Richard L. Apothaker, Northfield, N.J.

[73] Assignee: Kontes Glass Company, Vineland, N.J.

[21] Appl. No.: 165,383

[22] Filed: Jul. 3, 1980

[51] Int. Cl.³ .............................................. G02B 5/14
[52] U.S. Cl. ................................................ 250/227
[58] Field of Search ............. 250/227, 216, 571, 572; 350/96.24, 96.25

[56] References Cited

U.S. PATENT DOCUMENTS

| | | | |
|---|---|---|---|
| 3,535,537 | 10/1970 | Powell | 250/227 |
| 3,814,933 | 6/1974 | Weber | 250/227 |
| 3,937,558 | 2/1976 | Mukai et al. | 250/227 |
| 3,942,866 | 3/1976 | Roman | 250/227 |
| 3,953,730 | 4/1976 | Henry et al. | 250/227 |

*Primary Examiner*—David C. Nelms
*Attorney, Agent, or Firm*—James & Franklin

[57] ABSTRACT

A fiberoptic head includes, for each channel, two separate illuminating fiberoptic bundles and a light receiving fiberoptic bundle. Each illuminating fiberoptic bundle has its input end adjacent a light source. The light receiving fiberoptic bundle has its output end adjacent to a light detector. A block is provided with first, second and third passageways terminating at separate elongated apertures at the operative surface thereof. Each bundle extends through a different one of the passageways with the illuminating bundles terminating at apertures spaced from either side of the aperture for the light receiving bundle. The exterior apertures are located such that the projected illumination patterns overlap on the zone on the test surface from which the receiving bundle gathers light. The numerical aperture of the fibers in the light receivig bundle is selected to be less than the numerical aperture of the fiber in the illuminating bundle to increase the resolution and perceive only the center of the overlapping patterns of illumination.

3 Claims, 2 Drawing Figures

FIBEROPTIC HEAD WITH FIBER BUNDLES HAVING DIFFERENT NUMERICAL APERTURES

BACKGROUND OF THE INVENTION

The present invention relates to scanners and, more particularly, to a fiberoptic head for use in a scanner which enhances the accuracy of the device through increased resolution and the elimination of errors resulting from first order reflections.

A scanner, as the term is used herein, relates to any device in which the properties of a substance are analyzed by measuring effects on light transmitted through or reflected from the substance, as the substance and light source are moved relative to each other in a predetermined pattern. One common type of scanner is a densitometer, which is a device used in thin layer chromatography.

Thin layer chromatography is a chemical analytic technique whereby a chemical substance can be separated, identified, and quantitatively measured. This analytical technique is based on the well known physical property of chemical substances that different chemical substances in a mixture have different adsorption rates on a regular adsorbent material. The adsorbent material is utilized in the form of a thin layer or test surface adhering to a planar base, commonly called the "plate".

The mixture to be analyzed is placed in the form of a spot on the adsorbent material. A solvent is then caused to continuously migrate over the spot. The migration of the solution carries the substances present in the spot over certain distances on the adsorbent material, the distance which the substance is carried being dependent upon the chemical makeup of the specimen. As the substance is migrated along the adsorbent layer, the distance which each substance is carried is proportional to the partition coefficient of that substance.

Subsequent to completion of the separation by means of migration of the solvent, the spots are fixed in place on the adsorbent material by drying. After the spots are fixed, if they are not readily visible, they may be made visible by means of a developer. The developer can be ultraviolet light, radioactive materials, or chemicals sprayed on the chromographic area to induce co-reaction with the substances.

In one type of densitometer, reflected light from the spots on the plate is detected. Two separate channels, "read" and "reference", are employed. Separate beams of light are directed to different areas of the surface of the plate. During scanning, one of these beams (referred to as the "read" beam) is moved relative to the test surface to illuminate the spotted area, while the other beam (referred to as the "reference" beam) is moved relative to the test surface to illuminate an area of the plate which is free from spots. The reflected light from each of these beams is sensed by separate detecting means (read and reference) which may be any type of photosensitive signal generating means. The intensities of the light sensed by each of these detector means are compared and the difference in the reflected intensities is converted to an electrical output which may be quantitatively measured and recorded. Different wavelengths of light can be obtained by the use of filters such that optimum results can be obtained with a variety of different developer substances.

When sensing takes place, the sensing means and the thin layer chromatographic plate are moved relative to each other such that the plate is scanned. While scanning is taking place, the output signals generated by the densitometer may be quantitatively measured, as for example with a meter, and recorded, if desired.

The portion of the scanner which directs light to the test surface to illuminate same and senses light from the test surface and transfers same to the detecting means is called the head. Various different head configurations are well known in the art and have been utilized over many years.

In the simplest type of scanner head, two light paths are provided for each channel (read and reference). In each channel, light from a light source, such as an incandescent bulb or the like, is focused by means of a lens or reflected by means of a mirror along one of the paths such that same illuminates a portion of the test surface. Light reflected from the test surface passes through the second path and is focused by a lens or reflected by a second mirror, to the detector means.

More recently, however, scanners have utilized heads which employ fiberoptic bundles to more efficiently transfer light to and from the test surface. The head is provided with a single passageway for each channel (read and reference). For each channel, two fiberoptic bundles are provided which extend through the passageway. One of the bundles serves to illuminate an area on the test surface and the second bundle serves to gather light reflected from the test surface and transmit same to the detector means. Such a fiberoptic head is used in the scanner which forms the subject matter of U.S. Pat. No. 3,924,948 issued Dec. 9, 1975 to John Thoden and Theodore Wagner, and entitled: "Densitometer For Use In Quantitative Thin Layer Chromatographic Analysis". The reader is referred to that patent for a complete explanation of the manner in which a densitometer functions.

The conventional single passageway per channel fiberoptic scanner head configuration, as described above, has certain disadvantages which reduce the accuracy of the device. Because of the proximity of the output ends of the illuminating bundle and the input ends of the receiving bundle, incident reflection from the first or upper glass surface of the test plate often occurs. This reflection produces error signals many orders of magnitude higher than that of the data signals. The use of fiberoptic bundles with identical numerical apertures, as is often the case in the single passageway configuration, also increases the possibility of first order reflections, because the admittance angle of the receiving fibers is identical to the illumination angle of the illuminating fibers. Efforts to "randomize" the bundle to reduce this problem such that no two transmitting fibers are immediately adjacent each other and no two receiving fibers are immediately adjacent each other, have proved difficult, expensive, and subjective in nature because an orderly geometric pattern of fiber placement is required. Any deviation from this pattern causes "hot" or "cold" spots of transmitted or received light.

Moreover, the sharing of the same aperture by the illuminating and receiving fibers reduces the effective numerical aperture of both optical paths because the fiber ends must be closely packed. Simply enlarging the aperture so as to space the fiber ends from each other would increase the effective numerical aperture of the optical paths, but would decrease resolution, thereby reducing the accuracy of the device.

It is, therefore, a prime object of the present invention to provide a fiberoptic head for use in a scanner or the like, wherein errors due to first order reflection are reduced.

It is another object of the present invention to provide a fiberoptic head for use in a scanner or the like, wherein separate bundle termination apertures are provided which are spaced along the scanning direction.

It is another object of the present invention to provide a fiberoptic head for use in a scanner or the like, wherein overlapping illuminating patterns are projected on the test plate.

It is another object of the present invention to provide a fiberoptic bundle for use in a scanner or the like, wherein the resolution of the head is enhanced.

It is another object of the present invention to provide a fiberoptic bundle for use in a scanner or the like, wherein the fibers of the light receiving bundle are selected to have a numerical aperture which is lower than the numerical apertures of the fibers of the light transmitting bundles.

It is a further object of the present invention to provide a fiberoptic head for use in a scanner or the like, wherein the head is relatively simple and inexpensive to produce.

In accordance with the present invention, a head is provided for use in a scanner or the like, of the type having a light source and light detector means. The head comprises, for each channel, first and second illuminating fiberoptic bundles and a light receiving fiberoptic bundle. Each of the illuminating fiberoptic bundles has an input end situated to receive light from the light source. The light receiving fiberoptic bundle has an output end adjacent the detector means. A block is provided having an operative surface and first, second, and third passageways therein, terminating in separate apertures at the operative surface. Each of the bundles extends through a different one of the passageways with the output ends of the illuminating bundles and the input end of the receiving bundle at the respective apertures.

The apertures at which the first and second bundles terminate are preferably located on either side of, and spaced from, the aperture at which is situated the input end of the light receiving bundle. Each of the apertures has a substantially rectangular pattern, elongated along substantially parallel lines, transverse to the scanning direction.

Each of the first and second bundles projects a separate light pattern illuminating an area of the test surface. The location of the fiber output ends and the projected illumination angles are such that the illuminated areas on the test surface overlap to form an overlapping illuminated zone. The overlapping zone comprises the portion of the test surface area from which the light receiving bundle gathers light.

The fibers in the light receiving bundle are selected to have a numerical aperture which is lower than the numerical aperture of the fibers in either of the illuminating bundles. Thus, the ratio of the admittance angle of the light receiving bundle to the illumination angle of either of the illuminating bundles is selected to be greater than 1:1 and, preferably, between 1:2 and 1:10, depending upon the spacing between the ends of the bundles. This relationship enhances the resolution of the head.

Figure 2:
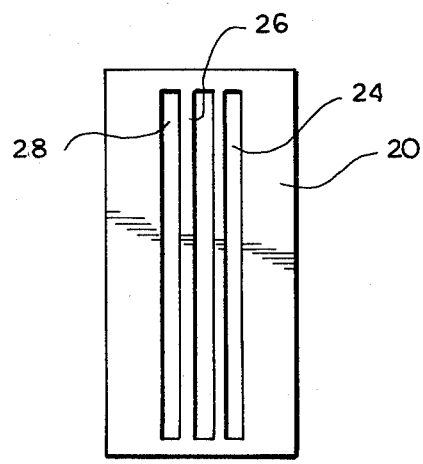

In accordance with the above, and to such other objects as may herein after appear, the present invention relates to a fiberoptic head for use in a scanner or the like, as described in detail in the following specification, and recited in the annexed claims, taken together with the accompanying drawings, wherein like numerals refer to like parts and in which:

FIG. 1 is a semi-schematic diagraom of the fiberoptic head of the present invention showing a side cross-sectional view of one channel (read or reference) thereof, and the light source and light detector means of a scanner in which same is used; and, FIG. 2 is a plan view of the operative surface of the head of the present invention.

As shown in FIG. 1, the head comprises a block 10 made of molded plastic or the like, having three separate passageways 12, 14 and 16 therethrough from the top surface 18 to the operative surface 20 thereof. FIG. 1 illustrates only a single channel (read or reference) of the scanner head. It should be appreciated that additional channels are normally provided and that same have a structure identical to the channel illustrated and, thus, have been omitted for simplicity. When in use, the operative surface 20 of head 10 is adjacent the upper surface of test plate 22. As best seen in FIG. 2, passageways 12, 14 and 16 terminate in separate rectangular apertures 24, 26 and 28 at the operative surface 20. Apertures 24, 26, 28 are elongated along spaced parallel lines in a direction substantially transverse to the scanning direction. The length of the apertures on any given head may vary and is limited only by the physical constraints of the scanner.

An illuminating fiberoptic bundle 30 is provided with its input end situated to receive light from a light source 32, which may comprise an incandescent bulb 34 or the like. The output end of fiberoptic bundle 30 terminates in aperture 24. Similarly, a second illuminating fiberoptic bundle 36 extends through passageway 16 in block 10 and has its input end situated to receive light from light source 32 and its output end terminating in aperture 28.

A light receiving bundle 38 extends down the center passageway 14 and has its input end at central aperture 26 and its output end adjacent a light detector means 40, such as a photoelectric cell 42 or the like. It will therefore be appreciated that the single aperture present in conventional devices of this type has been transversely partitioned into three separate spaced, equal sized apertures 24, 26, 28 elongated in a direction transverse to the scanning direction with the light receiving bundle aperture 26 being situated between the illuminating bundle apertures 24, 28.

Illuminating bundles 30 and 36 project light in a geometric pattern bounded by dashed lines 44. Apertures 24 and 28 are positioned such that the light beams projected by bundles 30 and 36 overlap in a pattern bounded by dashed lines 46. The overlapping pattern bounded by lines 46 illuminates a zone on the test plate. It is from this overlapping zone that receiving bundle 38 gathers light. This configuration substantially reduces first order reflections and, thus, the errors resulting therefrom.

The fibers in the light receiving fiberoptic bundle 38 are selected to have a numerical aperture which is lower than the numerical aperture of the fibers in either of the illuminating fiberoptic bundles 30 and 36, so as to restrict the field of view of the receiving bundle to the overlapping illuminated area. Preferably, the ratio of the admittance angle of the light receiving bundle to the illumination angle of either of the illuminating bundles is within the range of 1:2 and 1:10, depending upon the spacing between the apertures. For example, if the distance between apertures 24 and 26 and between apertures 26 and 28 are selected to be 0.25 millimeter, it has been found that selecting the ratio of admittance angle of the light receiving bundle to the illuminating angle of the light illuminating bundles to be 1:7.5 provides excellent results.

It should now be appreciated that the present invention relates to a fiberoptic head for use in a scanner or the like, wherein three separate fiberoptic bundles are utilized for each channel. The output ends of the illuminating bundles are spaced from, and situated on either side of the input end of the light receiving bundle, so as to create a zone on the test plate where the projected illumination patterns overlap. The area on the test surface from which light is gathered by the light receiving bundle is within the overlapping zone. This configuration reduces first order reflection and, thus, the errors resulting therefrom.

The numerical aperture of the fibers in the light receiving bundle is selected to be lower than the numerical aperture of the fibers in either of the illuminating bundles such that the admittance angle of the light gathering bundle is lower than the illumination angle of either of the illuminating bundles. By restricting the admittance angle of the light gathering bundle, the resolution of the head is enhanced.

While only a single embodiment of the present invention has been disclosed herein for purposes of illustration, it is obvious that many variations and modifications could be made thereto. It is intended to cover all of these variations and modifications which fall within the scope of the present invention, as defined by the following claims:

I claim:

1. A head for use in apparatus for scanning a test surface of the type having a light source and light detector means, said head comprising first and second illuminating fiberoptic bundles, each having an input end situated to receive light from the source and an output end illuminating an area on the test surface, said output ends being spaced from each other with said illuminated areas overlapping in a given zone, a light receiving fiberoptic bundle having an output end adjacent the detector means and an input end located between the output ends of said first and second bundles, such that said light receiving bundle gathers light from said given zone, wherein the numerical aperture of the fibers of said light receiving bundle is lower than the numerical aperture of the fibers in said first and second illuminating bundles.

2. The head of claim 1, wherein the ratio of the admittance angle of said light receiving bundle to the illumination angle of either of said first or second bundles is in the range between 1:2 to 1:10.

3. The head of claim 2, wherein said output ends of said illuminating bundles are spaced from said input ends of said light receiving bundle at a distance of approximately 0.25 millimeter and wherein said ratio is 1:7.5.

* * * * *